(12) United States Patent
Kim et al.

(10) Patent No.: US 12,285,401 B2
(45) Date of Patent: Apr. 29, 2025

(54) PHARMACEUTICAL COMPOSITION COMPRISING TRIMEBUTINE OR PHARMACEUTICALLY ACCEPTABLE SALT THEREOF AS AN ACTIVE INGREDIENT FOR PREVENTION OR TREATMENT OF CANCER

(71) Applicant: DAEGU-GYEONGBUK MEDICAL INNOVATION FOUNDATION, Daegu (KR)

(72) Inventors: Jun Woo Kim, Daegu (KR); Sang Hyun Min, Daegu (KR); Heejin Lee, Daegu (KR); Oh Bin Kwon, Daegu (KR)

(73) Assignee: DAEGU-GYEONGBUK MEDICAL INNOVATION FOUNDATION, Daegu (KR)

( * ) Notice: Subject to any disclaimer, the term of this patent is extended or adjusted under 35 U.S.C. 154(b) by 878 days.

(21) Appl. No.: 17/600,976

(22) PCT Filed: Apr. 6, 2020

(86) PCT No.: PCT/KR2020/004637
§ 371 (c)(1),
(2) Date: Nov. 8, 2021

(87) PCT Pub. No.: WO2020/204678
PCT Pub. Date: Oct. 8, 2020

(65) Prior Publication Data
US 2022/0193020 A1  Jun. 23, 2022

(30) Foreign Application Priority Data

Apr. 4, 2019 (KR) .................. 10-2019-0039613
Apr. 3, 2020 (KR) .................. 10-2020-0041000

(51) Int. Cl.
*A61K 31/24* (2006.01)
*A23L 33/10* (2016.01)
(Continued)

(52) U.S. Cl.
CPC .............. *A61K 31/24* (2013.01); *A23L 33/10* (2016.08); *A61K 45/06* (2013.01); *A61P 35/00* (2018.01)

(58) Field of Classification Search
CPC ...... A61K 31/24; A61K 31/704; A61K 45/06; A61K 2300/00; A61P 35/00
See application file for complete search history.

(56) References Cited

FOREIGN PATENT DOCUMENTS

| EP | 1110549 A1 | 6/2001 |
| EP | 2762155 A2 | 8/2014 |

(Continued)

OTHER PUBLICATIONS

Aydin et al., Vincristine in High-grade Glioma, Anticancer Research, vol. 30, 2303-2310, 2010 (Year: 2010).*

(Continued)

*Primary Examiner* — Sarah Pihonak
*Assistant Examiner* — Padmaja S Rao
(74) *Attorney, Agent, or Firm* — Klarquist Sparkman, LLP

(57) ABSTRACT

The present invention relates to a pharmaceutical composition comprising trimebutine as an active ingredient for prevention or treatment of cancer. Having an excellent effect of selectively inhibiting growth and proliferation of cancer stem cells, the pharmaceutical composition can suppress the recurrence, metastasis, and progression of cancer even when used alone. Thus, the composition can be advantageously used as a pharmaceutical composition for prevention or treatment of cancer or in combination with other agents.

7 Claims, 23 Drawing Sheets

(51) Int. Cl.
    *A61K 45/06*      (2006.01)
    *A61P 35/00*      (2006.01)

(56) References Cited

FOREIGN PATENT DOCUMENTS

| KR | 10-2014-0100416 A | 8/2014 |
| KR | 10-2016-0094861 A | 8/2016 |
| WO | 2016/044951 A1 | 3/2016 |
| WO | 2016/062285 A1 | 4/2016 |

OTHER PUBLICATIONS

Lee, H., et al., "Repositioning Trimebutine Maleate as a Cancer Treatment Targeting Ovarian Cancer Stem," Cells, vol. 10, Issue No. 4, Apr. 16, 2021, pp. 1-18.

Deok-Hun Kim, "Cancer stem cell theory and update in oral squamous cell carcinoma," Journal of the Korean Association of Oral and Maxillofacial Surgeons, vol. 37, Issue 2, 2011, pp. 97-108.

Distrutti, E. et al., A nitro-arginine ddrivative of trimebutine (NO2-Arg-Trim) attenuates pain induced by colorectal distension in conscious rats. Pharmacological research 2009 vol. 59, No. 5 pp. 319-329.

Fan, Y P et al. Trimebutine promotes glioma cell apoptosis as a potential anti-tumor agent, Frontriers in pharmacology. 2018. vol 9, article No. 664, pp. 1-9.

Ikram Jemel-Qualha, "Controversial effect on Erk activation of some cytotoxic drugs in human LOVO colon cancer cells," J Recept Signal Transduct Res, vol. 36, Issue 1, 2016, pp. 21-25.

International Search Report and Written Opinion received for PCT Patent Application No. PCT/KR2020/004637, mailed on Jul. 14, 2021, 16 pages (8 pages of English Translation and 8 pages of Original Document).

Reza Bayat Mokhtari, "Combination therapy in combating cancer," Oncotarget, vol. 8, Issue 23, 2017, pp. 38022-38043.

Shiraki, N. et al. Increase in doxorubicin cytotoxicity by inhibition of P-glycoprotein activity with Iomerizine Biological and pharmacecutical bulletin. 2001, vol. 24, No. 5, pp. 555-557.

* cited by examiner

A2780-SP

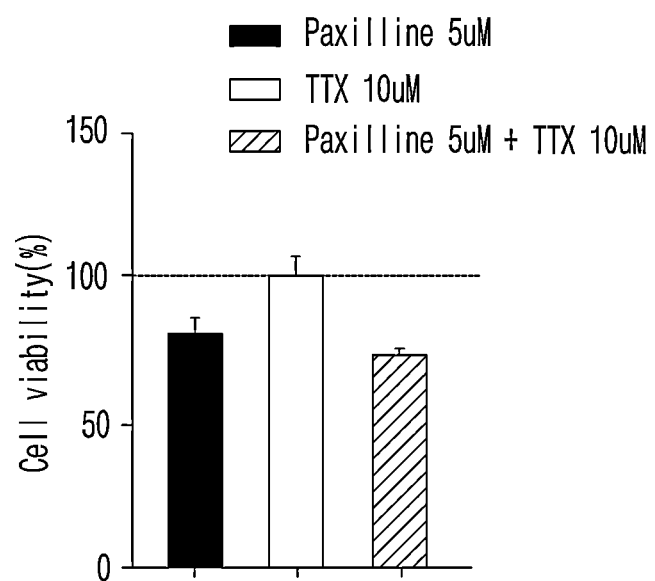

PHARMACEUTICAL COMPOSITION COMPRISING TRIMEBUTINE OR PHARMACEUTICALLY ACCEPTABLE SALT THEREOF AS AN ACTIVE INGREDIENT FOR PREVENTION OR TREATMENT OF CANCER

This patent application is a nationalization of and claims priority to PCT Application No. PCT/KR2020/004637 filed on Apr. 6, 2020 entitled "PHARMACEUTICAL COMPOSITION COMPRISING TRIMEBUTINE OR PHARMACEUTICALLY ACCEPTABLE SALT THEREOF AS ACTIVE INGREDIENT FOR PREVENTION OR TREATMENT OF CANCER," which claims priority to Korean Patent Application 10-2019-0039613, filed Apr. 4, 2019 and Korean Patent Application No. 10-2020-0041000 filed on Apr. 3, 2020. Each of the aforementioned applications is incorporated by reference herein in their entirety.

BACKGROUND OF THE INVENTION

1. Field of the Invention

The present invention relates to a pharmaceutical composition comprising trimebutine or a pharmaceutically acceptable salt thereof as an active ingredient for prevention or treatment of cancer.

2. Description of the Related Art

Stem cells refer to immature cells capable of self-renewal and differentiation into cells of each organ for organogenesis. Stem cells can be mainly classified into two types. Embryonic stem cells which are originated from the blastocyst can differentiate into any organ in the body. Stem cells for research are collected from the inner cell mass of the blastocyst with approximately 200 cells about 6 days after fertilization. Another type of stem cells is adult stem cells. Adult stem cells are the same as embryonic stem cells in that they are capable of self-renewal and differentiation, but adult stem cells differ from embryonic stem cells in that they mainly differentiate into cells within specific organs. A representative example of adult stem cells is hematopoietic stem cells.

Cancer stem cells, like stem cells, are capable of self-renewal and differentiation through asymmetric division, but unlike normal stem cells, they are cells that generate tumors due to a disorder in their ability to regulate division. Recent studies revealed that signaling pathways such as Notch, Sonic hedgehog (SHH), Wnt, β-catenin, phosphatase and tensin homolog [HONG7](PTEN), transforming growth factor (TGF)-β and Bmi-1 found in normal stem cells are altered in malignant tumors. Cancer stem cells show common characteristics with normal stem cells, such as high motility, progeny diversity, strong proliferation potential, vasculature, immature expression patterns, nestin, epidermal growth factor (EGF)-receptor, PTEN expression, Hedgehog signaling pathway activity, telomerase activity, Wnt signaling pathway activity, etc.

For the above reasons, the development of anticancer drugs targeting cancer stem cells is actively being made.

PRIOR ART REFERENCE

Patent Reference (Patent Reference 1) Korean Patent Publication No. 1020160094861

Non-Patent Reference (Non-patent Reference 1) J Korean Assoc Oral Maxillofac Surg 2011; 37:97

SUMMARY OF THE INVENTION

It is an object of the present invention to provide a pharmaceutical composition for preventing or treating cancer comprising trimebutine having an anticancer effect, a stereoisomer thereof, a hydrate thereof, or a pharmaceutically acceptable salt thereof as an active ingredient.

It is another object of the present invention to provide a combination preparation for preventing or treating cancer comprising the compound, a stereoisomer thereof, a hydrate thereof, or a pharmaceutically acceptable salt thereof and an anticancer agent.

It is another object of the present invention to provide a health functional food composition for preventing or ameliorating cancer comprising the compound, a stereoisomer thereof, a hydrate thereof, or a pharmaceutically acceptable salt thereof as an active ingredient.

It is another object of the present invention to provide a method for treating cancer comprising a step of administering the compound, a stereoisomer thereof, a hydrate thereof, or a pharmaceutically acceptable salt thereof to an individual or subject in need thereof.

It is another object of the present invention to provide the compound, a stereoisomer thereof, a hydrate thereof, or a pharmaceutically acceptable salt thereof for the treatment of cancer.

It is another object of the present invention to provide a use of the compound, a stereoisomer thereof, a hydrate thereof, or a pharmaceutically acceptable salt thereof for the preparation of a medicament for the treatment of cancer.

To achieve the above objects, in an aspect of the present invention, the present invention provides a compound represented by formula 1 below, a stereoisomer thereof, a hydrate thereof, or a pharmaceutically acceptable salt thereof.

[Formula 1]

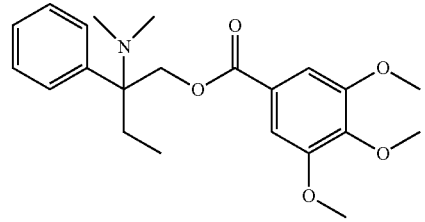 [SMILES: CCC(COC(=O)c1cc(OC)c(OC)c(OC)c1)(c1ccccc1)N(C)C]

In another aspect of the present invention, the present invention provides a combination preparation for preventing or treating cancer comprising the compound, a stereoisomer thereof, a hydrate thereof, or a pharmaceutically acceptable salt thereof and an anticancer agent.

In another aspect of the present invention, the present invention provides a health functional food composition for preventing or ameliorating cancer comprising the compound, a stereoisomer thereof, a hydrate thereof, or a pharmaceutically acceptable salt thereof as an active ingredient.

In another aspect of the present invention, the present invention provides a method for treating cancer comprising a step of administering the compound, a stereoisomer thereof, a hydrate thereof, or a pharmaceutically acceptable salt thereof to an individual or subject in need thereof.

In another aspect of the present invention, the present invention provides the compound, a stereoisomer thereof, a hydrate thereof, or a pharmaceutically acceptable salt thereof for the treatment of cancer.

In another aspect of the present invention, the present invention provides a use of the compound, a stereoisomer thereof, a hydrate thereof, or a pharmaceutically acceptable salt thereof for the preparation of a medicament for the treatment of cancer.

Advantageous Effect

The pharmaceutical composition comprising trimebutine of the present invention is excellent in inhibiting growth and proliferation of cancer stem cells even when used alone, and thus can suppress the recurrence, metastasis, and progression of cancer. Therefore, the composition can be effectively used as a pharmaceutical composition for prevention or treatment of cancer or in combination with other agents.

BRIEF DESCRIPTION OF THE DRAWINGS

FIG. 1A is a diagram showing the results of the treatment of trimebutine, the compound of Example 1, FIG. 1B is a diagram showing the results of the treatment of manidipine, the compound of Comparative Example 1, FIG. 1C is a diagram showing the results of the treatment of benidipine, the compound of Comparative Example 1, FIG. 1D is a diagram showing the results of the treatment of lacidipine, and FIG. 1E is a diagram showing the results of the treatment of lomerizine.

FIG. 2A is a diagram showing the results of the treatment of DAMGO (β-opioid receptor agonist), and FIG. 2B is a diagram showing the results of the treatment of Dynorphin A (κ-opioid receptor agonist).

FIG. 3A is a diagram showing the results of observing the current amplitude of the $BK_{Ca}$ channel, FIG. 3B is a diagram showing the results of observing the current amplitude of the Ca channel, and FIG. 3C is a diagram showing the results of observing the current amplitude of the Na channel.

FIGS. 6A to 6C are diagrams showing the sphere cell viability of A2780-SP cells when the pharmaceutical composition containing manidipine of Comparative Example 1 and the pharmaceutical composition of Comparative Example 2 were treated.

DESCRIPTION OF THE PREFERRED EMBODIMENTS

Figure 1A:
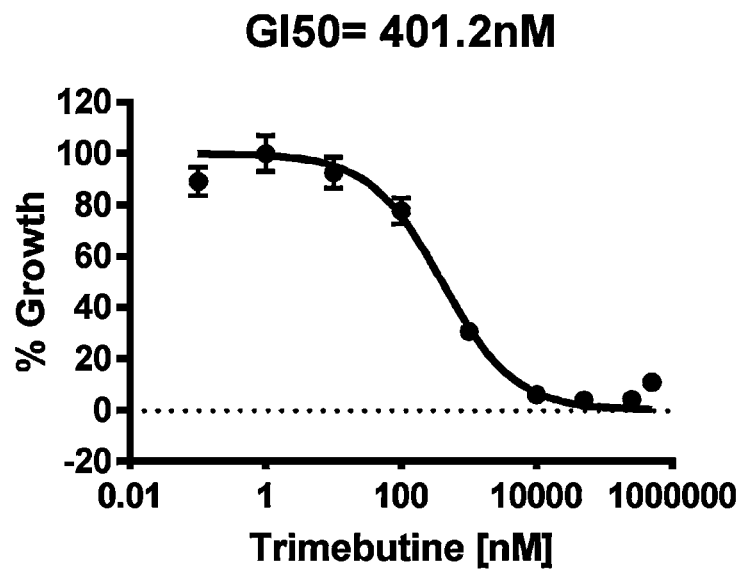
FIGS. 1A to 1E are diagrams showing the dose-response curves of A2780-SP cell (ovarian cancer stem cell) viability when the pharmaceutical compositions of Example 1 and Comparative Example 1 were treated.
Figure 1B:
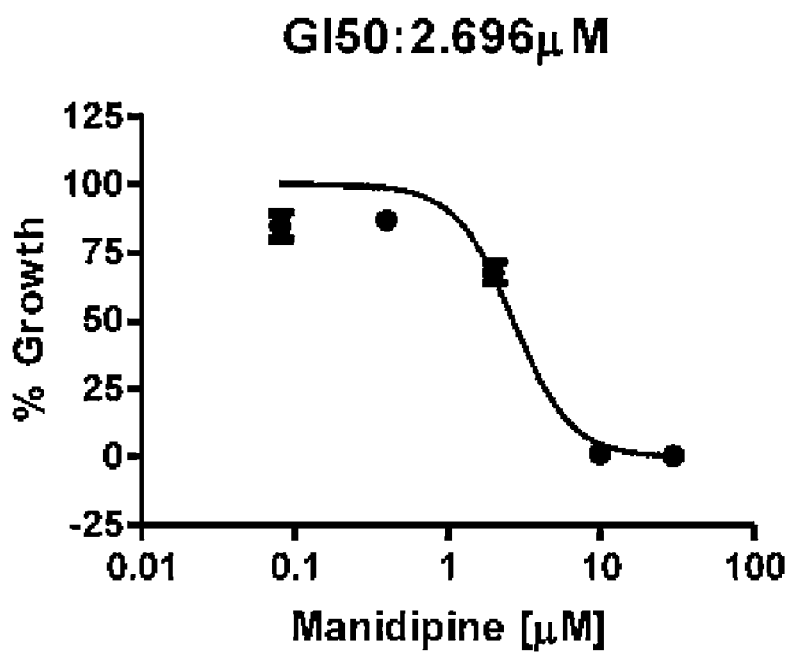
Figure 1C:
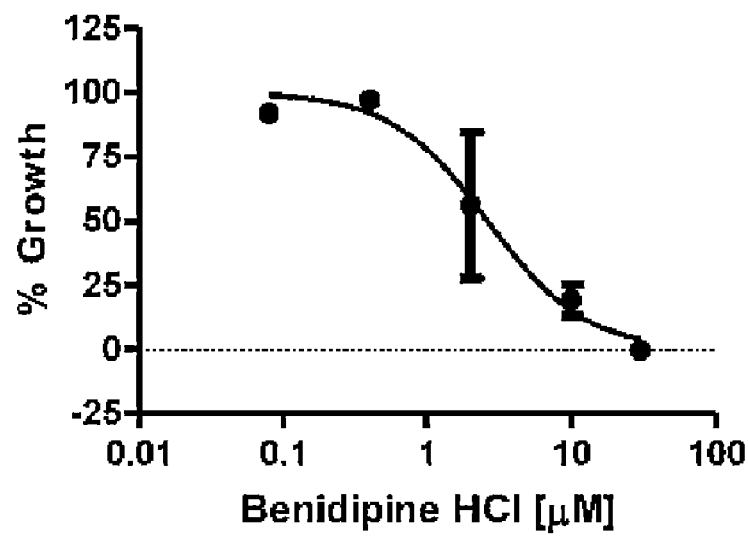
Figure 1D:
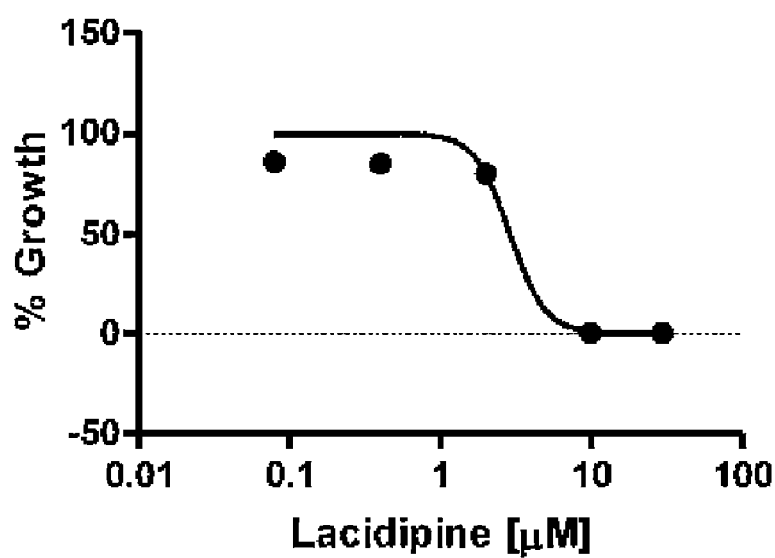
Figure 1E:
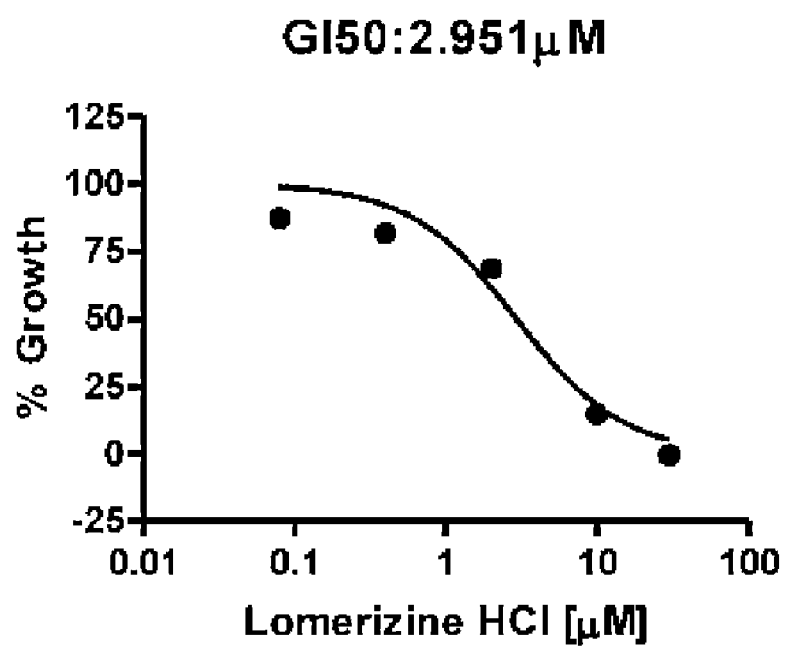

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely. In addition, the "inclusion" of an element throughout the specification does not exclude other elements, but may include other elements, unless specifically stated otherwise.

In an aspect of the present invention, the present invention provides a pharmaceutical composition for preventing or treating cancer comprising a compound represented by formula 1 below, a stereoisomer thereof, a hydrate thereof, or a pharmaceutically acceptable salt thereof as an active ingredient.

[Formula 1]

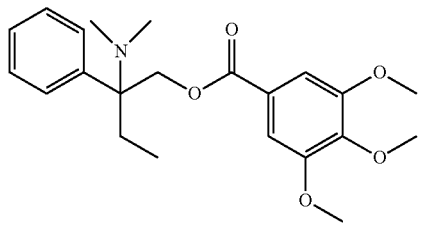

In another aspect of the present invention, the cancer may be at least one selected from the group consisting of benign astrocytoma, malignant astrocytoma, pituitary adenoma, meningioma, cerebral lymphoma, oligodendroglioma, intracranial tumor, ependymoma, brain stem tumor, laryngeal cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, abdominal tumor, stomach cancer, liver cancer, gallbladder cancer, biliary tract cancer, pancreatic cancer, small intestine cancer, colorectal cancer, anal cancer, bladder cancer, kidney cancer, penile cancer, prostate cancer, cervical cancer, endometrial cancer, ovarian cancer, uterine sarcoma, vaginal cancer, external genital cancer and skin cancer.

Also, the cancer can be ovarian cancer.

In another aspect of the present invention, the pharmaceutical composition can inhibit the proliferation of cancer stem cells.

In another aspect of the present invention, the pharmaceutical composition can inhibit the expression of at least one selected from the group consisting of CT3/4, NANOG, SOX2, ALDH, OCT4, CD133, pAKT, AKT, p-ERK, ERK, p-p38 and p 38.

As a result of measuring the anticancer effect of the pharmaceutical composition through various in vitro experiments, it was confirmed that the pharmaceutical composition had excellent anticancer effect since the composition reduced viability of cancer cells and cancer stem cells, inhibited proliferation thereof, suppressed sphere formation of cancer stem cells, and increased apoptosis of cancer stem cells.

Therefore, the pharmaceutical composition according to one aspect of the present invention can be effectively used as a pharmaceutical composition for preventing or treating cancer.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as trifluoroacetic acid, acetate, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

In addition, a pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an optical isomer, or a hydrate possibly produced from the same.

The compound represented by formula 1 or the pharmaceutically acceptable salt thereof can be administered orally or parenterally in various formulations at the time of clinical administration. The compound represented by formula 1 or the pharmaceutically acceptable salt thereof can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. These solid formulations are prepared by mixing the compound or the pharmaceutically acceptable salt thereof of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

To prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides a combination preparation for preventing or treating cancer comprising a compound represented by formula 1 below, a stereoisomer thereof, a hydrate thereof, or a pharmaceutically acceptable salt thereof and an anticancer agent.

In another aspect of the present invention, the cancer may be at least one selected from the group consisting of benign astrocytoma, malignant astrocytoma, pituitary adenoma, meningioma, cerebral lymphoma, oligodendroglioma, intracranial tumor, ependymoma, brain stem tumor, laryngeal cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, abdominal tumor, stomach cancer, liver cancer, gallbladder cancer, biliary tract cancer, pancreatic cancer, small intestine cancer, colorectal cancer, anal cancer, bladder cancer, kidney cancer, penile cancer, prostate cancer, cervical cancer, endometrial cancer, ovarian cancer, uterine sarcoma, vaginal cancer, external genital cancer and skin cancer.

Also, the cancer can be ovarian cancer.

In another aspect of the present invention, the combination preparation can inhibit the proliferation of cancer stem cells.

In another aspect of the present invention, the combination preparation can inhibit the expression of at least one selected from the group consisting of CT3/4, NANOG, SOX2, ALDH, OCT4, CD133, pAKT, AKT, p-ERK, ERK, p-p38 and p 38.

The term "anticancer agent" refers to a generic term for known agents used in conventional cancer treatment that act on various metabolic pathways of cancer cells and exhibit cytotoxicity or cytostatic effects on cancer cells, and includes all of the antimetabolites, plant alkaloids, topoisomerase inhibitors, alkylating agents, anticancer antibiotics, hormones and other drugs developed so far.

In an aspect of the present invention, the anticancer agent may be at least one selected from the group consisting of doxorubicin, paclitaxel, vincristine, daunorubicin, vinblastine, actinomycin-D, docetaxel, etoposide, teniposide, bisantrene, homoharringtonine, Gleevec (STI-571), cisplatin, 5-fluorouracil, adriamycin, methotrexate, busulfan, chlorambucil, cyclophosphamide, melphalan, nitrogen mustard and nitrosourea.

In another aspect of the present invention, the present invention provides a health functional food composition for preventing or ameliorating cancer comprising cancer comprising a compound represented by formula 1 below, a stereoisomer thereof, a hydrate thereof, or a pharmaceutically acceptable salt thereof as an active ingredient.

[Formula 1]

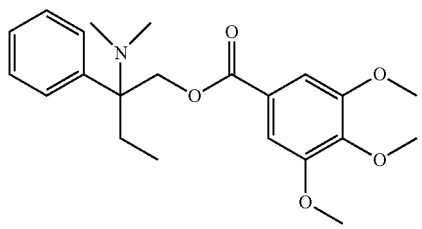

[Formula 1]

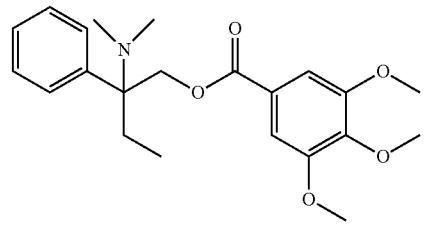

In another aspect of the present invention, the cancer may be at least one selected from the group consisting of benign astrocytoma, malignant astrocytoma, pituitary adenoma, meningioma, cerebral lymphoma, oligodendroglioma, intracranial tumor, ependymoma, brain stem tumor, laryngeal cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, abdominal tumor, stomach cancer, liver cancer, gallbladder cancer, biliary tract cancer, pancreatic cancer, small intestine cancer, colorectal cancer, anal cancer, bladder cancer, kidney cancer, penile cancer, prostate cancer, cervical cancer, endometrial cancer, ovarian cancer, uterine sarcoma, vaginal cancer, external genital cancer and skin cancer.

Also, the cancer can be ovarian cancer.

The compound represented by formula 1 of the present invention can be used as a food additive. In that case, the compound represented by formula 1 of the present invention can be added as it is or as mixed with other food components according to the conventional method. The mixing ratio of active ingredients can be regulated according to the purpose of use (prevention or amelioration). In general, the compound of the present invention is preferably added to food or beverages by 0.1~90 weight part for the total weight of the food or beverages. However, if long term administration is required for health and hygiene or regulating health condition, the content can be lower than the above but higher content can be accepted as well since the compound of the present invention has been proved to be very safe.

The health beverage composition of the present invention can additionally include various flavors or natural carbohydrates, etc, like other beverages. The natural carbohydrates above can be one of monosaccharides such as glucose and fructose; disaccharides such as maltose and sucrose; polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition of the invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include natural fruit juice, fruit beverages and fruit flesh addable to vegetable beverages.

In another aspect of the present invention, the present invention provides a method for treating cancer comprising a step of administering the compound, a stereoisomer thereof, a hydrate thereof, or a pharmaceutically acceptable salt thereof to an individual or subject in need thereof.

In another aspect of the present invention, the present invention provides the compound, a stereoisomer thereof, a hydrate thereof, or a pharmaceutically acceptable salt thereof for the treatment of cancer.

In another aspect of the present invention, the present invention provides a use of the compound, a stereoisomer thereof, a hydrate thereof, or a pharmaceutically acceptable salt thereof for the preparation of a medicament for the treatment of cancer.

Since the compound, a stereoisomer thereof, a hydrate thereof, or a pharmaceutically acceptable salt thereof provided in one aspect of the present invention can significantly inhibit the proliferation of cancer cells and cancer stem cells, it can be effectively used as a pharmaceutical composition for preventing or treating cancer, which is supported by the Examples and Experimental Examples described below.

Hereinafter, the present invention will be described in detail by the following examples and experimental examples.

However, the following examples and experimental examples are only for illustrating the present invention, and the contents of the present invention are not limited thereto.

Example 1: Pharmaceutical Composition Comprising Trimebutine

Trimebutine having the following structure, known as an opioid receptor agonist or a Ca channel blocker, was prepared.

(place of purchase: Sigma-Aldrich)

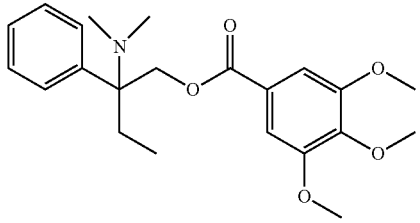

Comparative Example 1: Pharmaceutical Composition Comprising Ca Channel Blocker

Trimebutine of the present invention is well known as a Ca channel blocker. For the comparative experiment, the following four test substances were prepared as Ca channel blockers.

The substance names, chemical structures, and places of purchase of the comparative test substances used are shown in Table 1 below.

TABLE 1

| Name | Chemical structure | Place of purchase |
|---|---|---|
| 1 Manidipine | 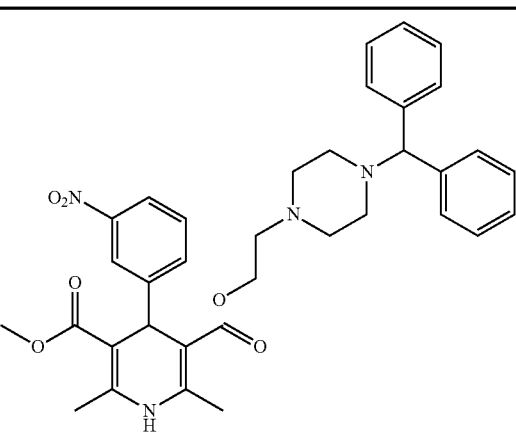 | Selleckchem |
| 2 Benidipine | 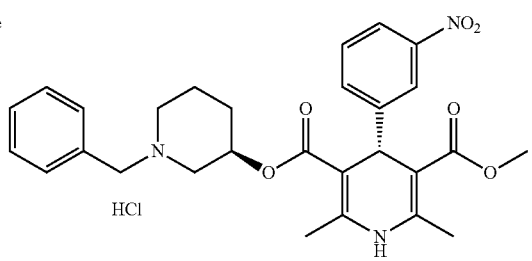 | Tocris |
| 3 Lacidipine | 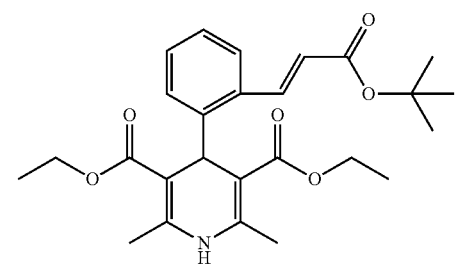 [SMILES: CCOC(=O)C1=C(C)NC(C)=C(C(=O)OCC)C1c1ccccc1/C=C/C(=O)OC(C)(C)C] | Sigma |
| 4 Lomerizine | 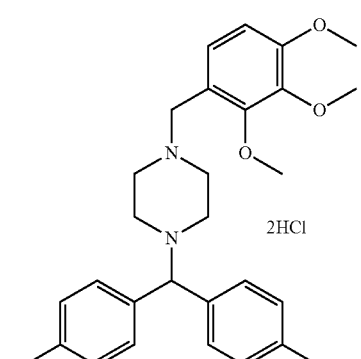 | Selleckchem |

Comparative Example 2: Pharmaceutical Composition Comprising K and Na Channel Blocker Trimebutine of the present invention is well known as a $BK_{Ca}$ and Na channel blocker. For the comparative experiment, Paxilline as a $BK_{Ca}$ channel blocker and Tetrodotoxin as a Na channel blocker were prepared.

Comparative Example 3: Pharmaceutical Composition Comprising Opioid Receptor Agonist Trimebutine of the present invention is well known as an opioid receptor agonist. For the comparative experiment, DAMGO (μ-opioid receptor agonist) and Dynorphin A (κ-opioid receptor agonist) were prepared as opioid receptor agonists.

<Experimental Protocol>
1. Cell Viability Assay

A2780-SP cells (ovarian cancer stem cells) were plated in an ultra-low attachment round bottom 96-well plate (Corning) at the density of 1,500 viable cells per well and cultured in a cancer stem cell medium. The cancer stem cell medium is composed of a neurobasal medium supplemented with 20 ng/ml of bFGF, 10 ng/ml of EGF, 2.5 ng/ml of amphotericin B, HEPES, Glutamax and B27. On the next day of culture, the cells were treated with the compounds of Example 1 and Comparative Examples 1 to 3 and further cultured for 8 days. The medium containing the compound was added once again on day 4 of culture.

Sphere cell viability was evaluated by Cell-titer Glo (Promega, WC, USA), and luciferase activity was detected using a Tecan plate reader (Biocompare, USA).

A2780-SP cells (ovarian cancer stem cells) were plated in a 96-well plate at the density of 3,500 viable cells per well and cultured in RPMI-1640 medium supplemented with 10% FBS and 1% penicillin/streptomycin. On the next day of culture, the cells were treated with the compounds of Example 1 and Comparative Examples 1 to 3 and further cultured for 3 days. Sphere cell viability was evaluated by Cell-titer Glo (Promega, WC, USA), and luciferase activity was detected using a Tecan plate reader (Biocompare, USA).

2. Whole Cell Patch Clamp Recording

The cells (ovarian cancer cells (A2780) and ovarian cancer stem cells (A2780-SP)) prepared in advance on cover glasses were transferred to a recording chamber and an external solution was continuously circulated. The composition of the external solution for measuring $Na^+$ and $Ca^{2+}$ currents was 143 mM NaCl, 5.6 mM KCl, 10 mM $CaCl_2$, 2 mM $MgCl_2$, 10 mM HEPES and 5 mM glucose, and the pH was adjusted to 7.4 using NaOH. For $Ca^{2+}$ current measurement, 1 nM tetrodotoxin and 10 mM tetraethylammonium were added to the external solution. In addition, for $Na^+$ current measurement, the same amount of $MgCl_2$ and 10 mM tetraethylammonium were added instead of 10 mM $CaCl_2$).

The composition of the internal pipette solution for whole cell patch was 140 mM CsCl, 2 mM $MgCl_2$, 3 mM Mg-ATP, 5 mM HEPES and 1.1 mM EGTA, and the pH was adjusted to 7.2 using CsOH. The composition of the external solution for measuring BK channel current was 140 mM NaCl, 5.4 mM KCl, 1.8 mM $CaCl_2$, 1 mM $MgCl_2$, 10 mM HEPES and 10 mM glucose, and the pH was adjusted to 7.3 using NaOH. The composition of the internal pipette solution for whole cell patch to the BK channel was 20 mM KCl, 110 mM K-aspartate, 1 mM $MgCl_2$, 10 mM HEPES, 5 mM EGTA, 0.1 mM GTP, 5 mM $Na_2$-phosphocreatine and 5 mM Mg-ATP, and the pH was adjusted to 7.2 using KOH.

Each ion current was measured using Axopatch 700B, DigiData 1440A and pClamp 10.4 in a voltage clamp mode, and the basic membrane potential was set at −70 mV. $Ca^{2+}$ current was measured by increasing the membrane voltage by 10 mV starting at −70 mV, and $Na^+$ current was measured by increasing the membrane voltage by 10 mV starting at −90 mV. $K^+$ current of the BK channel was measured by increasing the membrane voltage by 10 mV starting at −80 mV. After the normal current was measured, 10 μM of trimebutine of Example 1 was treated for 5 minutes, and the same voltage change was applied to measure the change in the amount of current resulting therefrom. The access resistance (Ra) value of the whole cell patch clamp was used as 10-20 MΩ.

3. Western Blotting

A2780-SP cells (ovarian cancer stem cells) were plated in an ultra-low attachment 6-well plate (Corning) at the density of $4 \times 10^5$ viable cells per well and cultured in a cancer stem cell medium. On the next day of culture, the medium was replaced with NBM (Neuro Basal Medium), and the cells were cultured for 16 hours in starvation. Then, the cells were treated with the compound of Example 1 at the concentration of 1 μM or 10 μM for 1 hour. The medium was replaced with a cancer stem cell medium containing the compound, and the cells were collected and cultured for an additional 30 minutes before being lysed in RiPA buffer. The extracted protein was separated by SDS-PAGE gel and transferred to a PVDF membrane for Western blotting. After blocking with 5% skim milk, the membrane was incubated with primary antibodies in a blocking buffer at 4° C. overnight, and then incubated with HRP-conjugated secondary antibodies at room temperature for 2 hours.

The primary antibodies used herein were as follows: anti-phospho-AKT (Ser473)(clone 193H12, Cell Signaling), anti-AKT (rabbit polyclonal, Cell Signaling), anti-phospho-ERK (Thr202/Tyr204) (clone 20G11, Cell Signaling), anti-ERK (rabbit monoclonal, Cell Signaling), anti-phospho-p38 (rabbit monoclonal, Cell Signaling), anti-p38 (rabbit monoclonal, Cell Signaling), anti-OCT3/4 (mouse monoclonal, Santa Cruz), anti-NANOG (rabbit monoclonal, Cell Signaling), anti-SOX2 (rabbit monoclonal, Cell signaling), anti-ALDH1 (mouse monoclonal, BD), anti-CD133 (rabbit monoclonal, Abcam), anti-GAPDH (mouse monoclonal, Santa Cruz) anti-beta catenin (Cell signaling), anti-phospho-beta catenin (S552) (Cell signaling) and anti-histone H3 (Cell signaling).

The secondary antibodies used herein were as follows: Goat anti-mouse IgG-HRP (Bioss) and Goat anti-rabbit IgG-HRP (Bioss).

Signals were developed on an enhanced chemiluminescence HRP substrate (Bio-Rad) and detected using LAS-3000 mini (Fuji film). The signals were quantified using Image J software (NIH Image).

4. β-catenin S552 phosphorylation and translocation experiments

A2780-SP cells (ovarian cancer stem cells) were plated in an ultra-low attachment round bottom 6-well plate (Corning) at the density of $4 \times 10^5$ viable cells per well and cultured in a cancer stem cell medium (CM). The cancer stem cell medium is composed of a neurobasal medium supplemented with 20 ng/ml of bFGF, 10 ng/ml of EGF, 2.5 ng/ml of amphotericin B, HEPES, Glutamax and B27. On the next day of culture, the cells were treated with the compound at the concentration of 1 μM or 10 μM for 24 hours. The control group was treated in the same manner as above for 24 hours with a neurobasal medium (NBM) and a cancer stem cell medium (CM) containing DMSO.

To measure the degree of phosphorylation of β-catenin S552, 100 μl of RIPA buffer (containing 1× protease inhibitor and phosphatase inhibitor) was added to the prepared cells, and the cells were disrupted by shaking once every 5 minutes for a total of 15 minutes. The disrupted cells were centrifuged at 13,000 rpm for 15 minutes to collect only the supernatant protein, and the obtained protein was quantified using a BCA protein quantification kit (Pierece, MA, USA), and a total of 15 μg of the protein was used for Western blotting. NE-PER Nuclear and Cytoplasmic Extraction Reagents (Thermoscientific, #78833) were used to separate cytoplasmic and nuclear proteins. 100 μl of Cytoplasmic Extraction Reagent I was added to the prepared cells, and the cells were disrupted on ice by shaking for 10 minutes. After adding 5.5 μl of Cytoplasmic Extraction Reagent II, the cells were disrupted on ice by shaking for 1 minute. The disrupted cells were centrifuged at 16,000 g for 5 minutes to separate the supernatant cytoplasmic proteins. 50 µl of Nuclear Extraction Reagent was added to the disrupted cells remaining after the separation of the supernatant (pellet), and the cells were disrupted on ice by shaking once every 10 minutes for a total of 40 minutes. The disrupted cells were centrifuged at 16,000 g for 10 minutes to separate the supernatant nuclear proteins. The obtained cytoplasmic and nuclear proteins were quantified using a BCA protein quantification kit (Pierece, MA, USA), and a total of 15 µg of the cytoplasmic protein and 8 µg of the nuclear protein were used for Western blotting. The Western blotting method is the same as the Western blotting method described in Experimental Protocol 3 above.

5. Animal Experiment

In order to confirm the inhibitory effect of the pharmaceutical composition of Examples of the present invention in the ovarian cancer stem cell tumor model, each nude mouse was subcutaneously inoculated with $2\times10^6$ A2780-SP (ovarian cancer stem cell line) cells. After the implantation, the size of tumor formation was measured using a caliper. When the tumor volume became 100 mm$^3$ or more, the experimental group was divided into the control group (vehicle) and the pharmaceutical composition of Examples of the present invention treated group (3 mg/kg of trimebutine) and the drug was administered to confirm the effect of the drug. The drug was administered 10 times a day through intraperitoneal administration, and the size of the tumor and the weight of the mouse were measured at intervals of 3 to 4 days. Then, all mice were euthanized on the day of the end of the experiment, and finally the size of the tumor and the weight were measured.

Experimental Example 1: Viability Analysis of Cancer Cells and Cancer Stem Cells <1-1> Analysis of Inhibitory Effect of Ca Channel Blocker on Growth of Cancer Cells and Cancer Stem Cells Trimebutine of the present invention is well known as a Ca channel blocker.

Therefore, in Experimental Example <1-1>, in order to analyze the viability of cancer cells and cancer stem cells according to the treatment of the pharmaceutical composition containing the trimebutine of the present invention or the Ca channel blocker of Comparative Example 1, cell viability analysis was performed by measuring the $GI_{50}$ values of the pharmaceutical compositions of Example 1 and Comparative Example 1 for cancer cells and cancer stem cells. The specific experimental method is the same as the cell viability analysis method described in Experimental Protocol 1, and the results are shown in FIGS. 1A to 1G and Table 2.

FIGS. 1A to 1E are diagrams showing the results of measuring the maximum concentration at the moment when the cell proliferation of A2780-SP (ovarian cancer stem cells) was reduced by half and the dose-response curves of A2780-SP cell viability when the pharmaceutical compositions of Example 1 and Comparative Example 1 were treated.

Figure 1F:
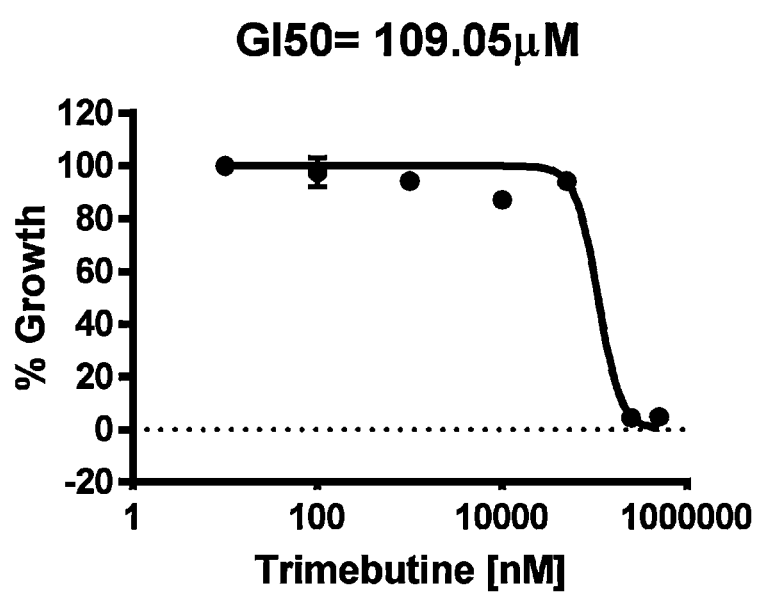
FIGS. 1F and 1G are diagrams showing the dose-response curves of A2780 cell (ovarian cancer cell) viability when the pharmaceutical compositions containing trimebutine of Example 1 and manidipine of Comparative Example 1 were treated, respectively.
Figure 1G:
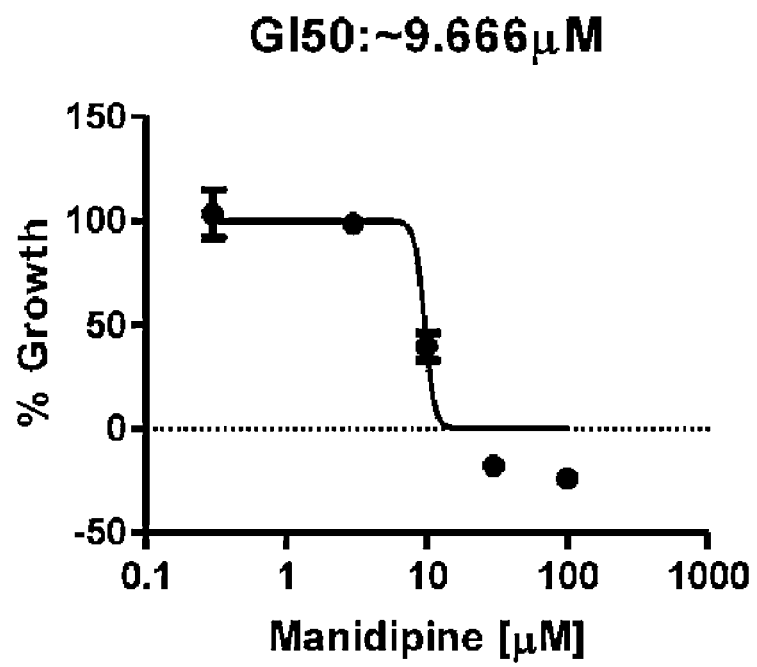

FIGS. 1F and 1G are diagrams showing the results of measuring the maximum concentration at the moment when the cell proliferation of A2780 (ovarian cancer cells) was reduced by half and the dose-response curves of A2780 cell viability when the compound of Example 1 and the manidipine compound of Comparative Example 1 were treated.

TABLE 2

| Compound | GI50 (A2780-SP) | GI50 (A2780) |
|---|---|---|
| Example 1 | 401.2 nM | — |
| Comparative Example 1 (manidipine) | 2.696 µM | ~9.666 µM |
| Comparative Example 1 (benidipine) | 2.645 µM | |
| Comparative Example 1 (lacidipine) | 2.899 µM | |
| Comparative Example 1 (lomerizine) | 2.951 µM | |

As shown in FIGS. 1A to 1E, it was confirmed that the pharmaceutical compositions of Example 1 and Comparative Example 1 reduced the viability of A2780-SP cells (ovarian cancer stem cells) dose-dependently. In particular, the GI50 value of the compound of Example 1, trimebutine, was 401.2 nM, confirming that it exhibited a superior cancer stem cell growth inhibitory effect than the calcium blocker of Comparative Example 1.

As shown in FIGS. 1F and 1G, it can be seen that the pharmaceutical composition of Example 1 promoted apoptosis of cancer stem cells rather than cancer cells with excellent selectivity when compared with the results of FIGS. 1A to 1E.

Therefore, it was confirmed that the pharmaceutical composition comprising trimebutine of the present invention had an anticancer effect as it exhibited a growth inhibitory effect on cancer stem cells.

<1-2> Analysis of Inhibitory Effect of Opioid Receptor Agonist on Growth of Cancer Cells and Cancer Stem Cells Trimebutine of the present invention is well known as an opioid receptor agonist.

Therefore, in Experimental Example <1-2>, in order to analyze the sphere viability of cancer stem cells according to the treatment of the pharmaceutical composition containing the trimebutine of the present invention or the opioid receptor agonist of Comparative Example 3, sphere cell viability analysis was performed by measuring the G150 values of the pharmaceutical compositions of Example 1 and Comparative Example 3 for cancer cells and cancer stem cells. Sphere cell viability of ovarian cancer stem cells was measured when the compound of Comparative Example 3 were treated at the concentrations of 0 µM, 0.2 µM, 1 µM and 5 µM. The experiment was performed with 1500 cells for 7 days by the Cell titer Glo method. The specific experimental method is the same as the cell viability analysis method described in Experimental Protocol 1, and the results are shown in FIGS. 2A and 2B.

Figure 2A:
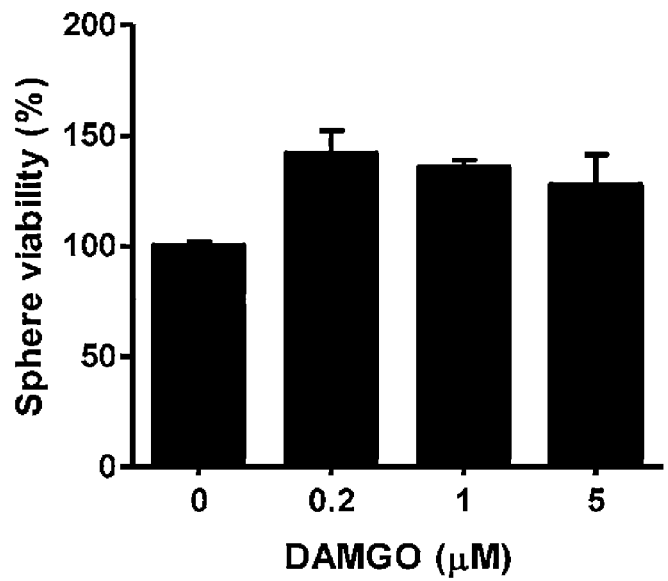
FIGS. 2A and 2B are diagrams showing the sphere cell viability of A2780-SP cells when the pharmaceutical composition of Comparative Example 3, an opioid receptor agonist, was treated.
Figure 2B:
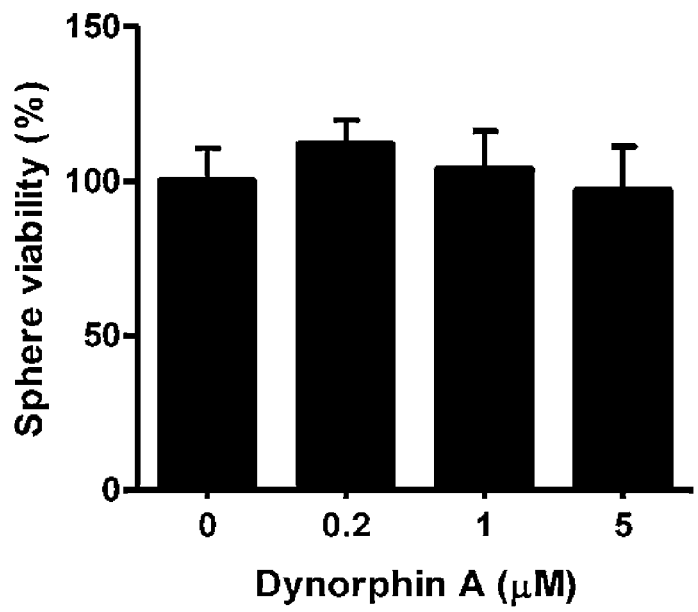

As shown in FIGS. 2A and 2B, it was confirmed that the opioid receptor agonist of Comparative Example 3 had no effect of inhibiting the viability of ovarian cancer stem cells. On the other hand, as shown in FIGS. 1A to 1E, it was confirmed that trimebutine, a well-known opioid receptor agonist, a well-known opioid receptor agonist, showed an excellent effect of inhibiting the survival of ovarian cancer stem cells when it was treated to ovarian cancer stem cells.

Therefore, it was confirmed that the anticancer effect of the pharmaceutical composition comprising trimebutine of the present invention through the cancer stem cell growth inhibitory effect was not related to the opioid receptor.

Experimental Example 2: Analysis of Correlation Between Cancer Stem Cells and $BK_{Ca}$, Ca and Na Channel Activity <2-1> Whole Cell Patch Clamp Recording In order to evaluate the inhibitory effect of the pharmaceutical composition containing trimebutine of the present invention on $BK_{Ca}$, Ca and Na channels in ovarian cancer stem cells (A2780-SP), the following experiment was performed. The specific experimental method is the same as the whole cell patch clamp recording method described in Experimental Protocol 2, and the results are shown in FIGS. 3A to 3C.

Figure 3A:
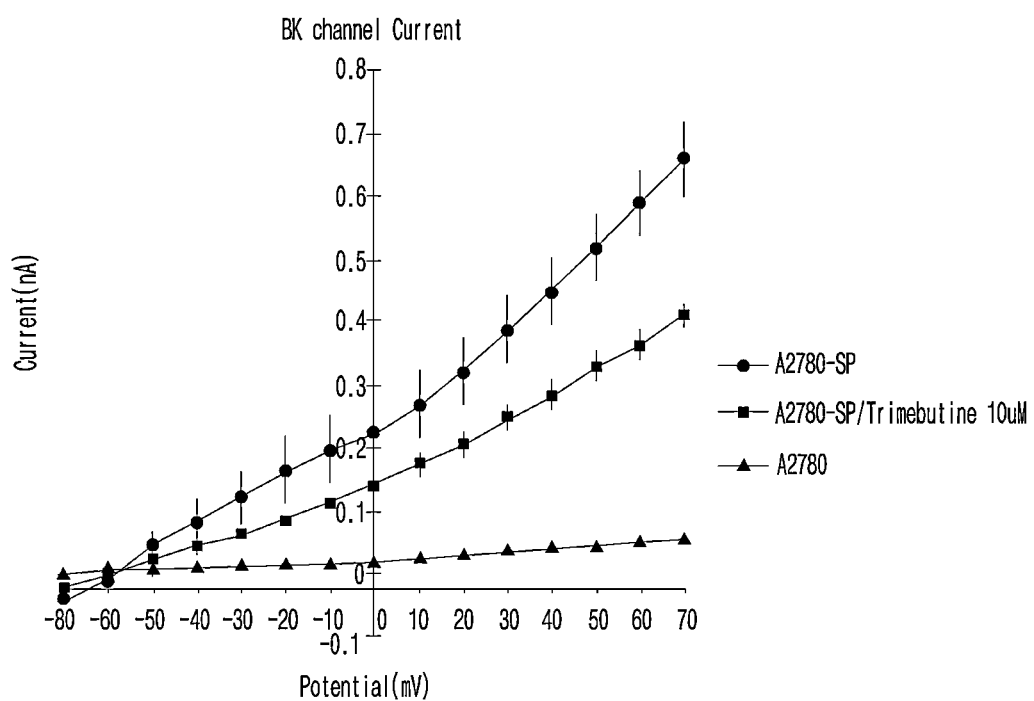
FIGS. 3A to 3C are diagrams showing that the current amplitudes of the channels were reduced when A2780-SP cells were treated with the pharmaceutical composition of Example 1.
Figure 3B:
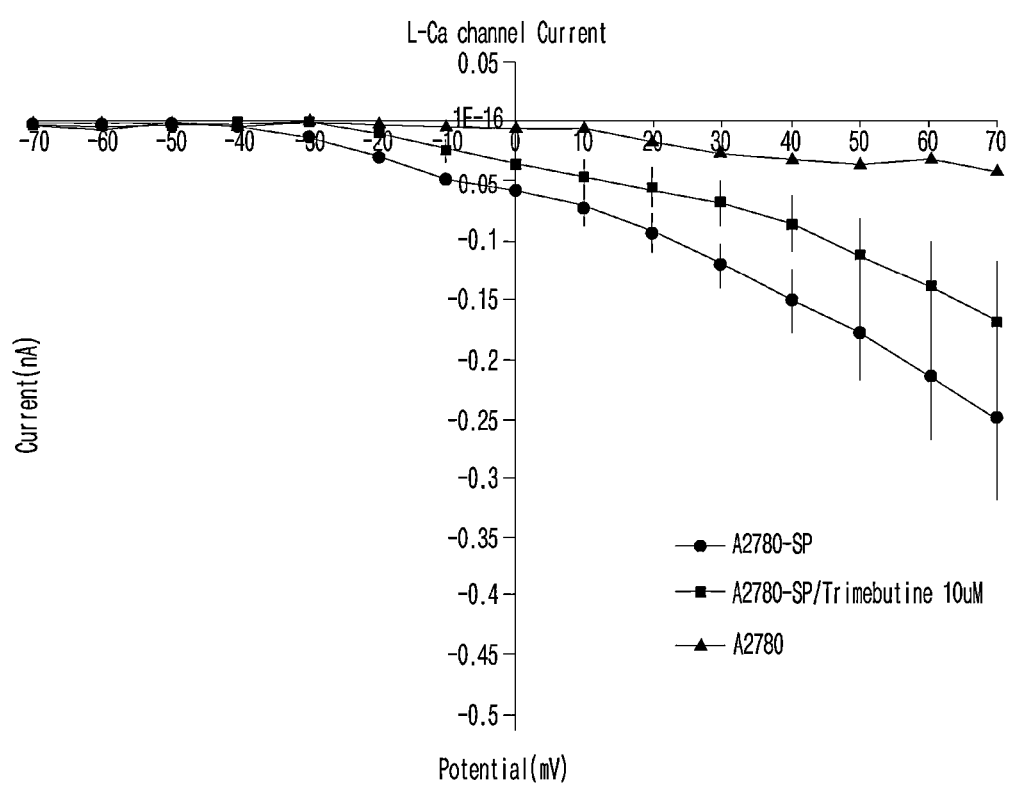
Figure 3C:
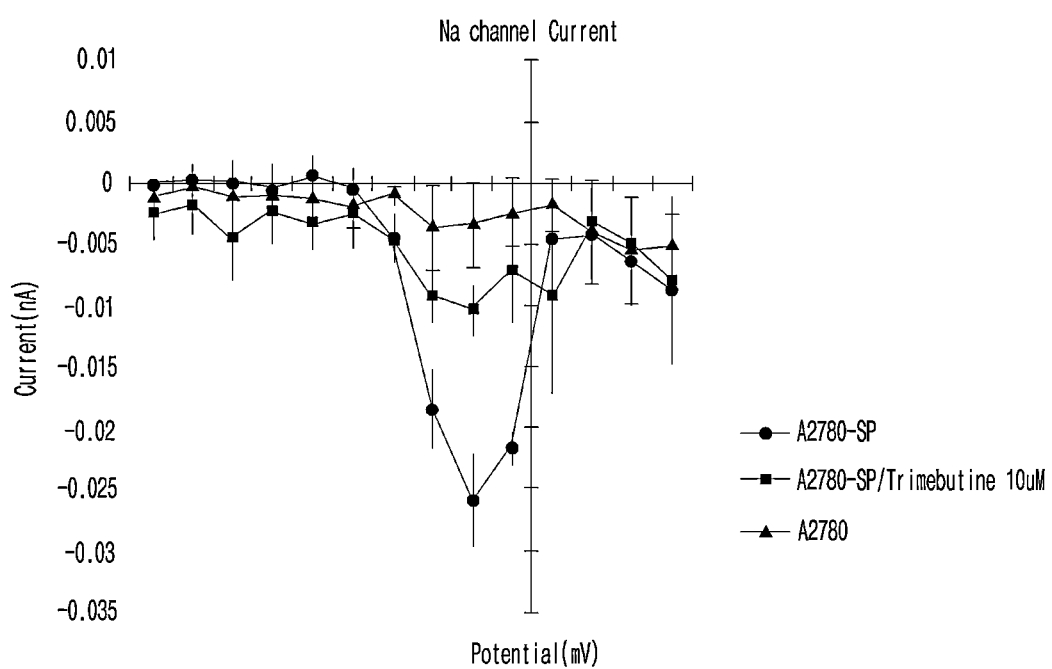

FIGS. 3A to 3C are graphs showing that the amplitudes of Ca activated $BK_{Ca}$ channel (FIG. 3A), L-type Ca channel (FIG. 3B) and Na channel (FIG. 3C) were reduced when A2780-SP cells were treated with the pharmaceutical composition of Example 1.

As shown in FIGS. 3A to 3C, the amplitudes of $BK_{Ca}$ channel (Ca dependent potassium channel current) current, Ca channel current (calcium channel current) and Na channel current (sodium channel current) were bigger in ovarian cancer stem cells (A2780-SP) than in ovarian cancer cells (A2780). When A2780-SP cells were treated with the compound of Example 1, the pharmaceutical composition containing trimebutine of the present invention, having inhibitory effect on $BK_{Ca}$, Ca and Na channels, the amplitudes of $BK_{Ca}$, Ca and Na currents were remarkably suppressed.

The above results indicate that the pharmaceutical composition containing trimebutine of the present invention inhibits the stemness of cancer stem cells, which is a major factor showing resistance to existing drugs, through inhibition of the $BK_{Ca}$, Ca and Na channels overexpressed in cancer stem cells, and suggest that it can induce apoptosis.

Through this, it can be seen that the pharmaceutical composition containing trimebutine of the present invention can be effectively used for cancer treatment by inhibiting cancer recurrence, metastasis and progression.

<2-2> Analysis of Inhibitory Effect of $BK_{Ca}$ and Na Channel Blockers on Cancer Cell and Cancer Stem Cell Growth Trimebutine of the present invention is well known as a $BK_{Ca}$ channel blocker (Ca dependent potassium channel blocker) and Na channel inhibitor (sodium channel blocker).

Therefore, in Experimental Example <2-2>, cell viability analysis was performed by measuring the $IC_{50}$ values obtained by analyzing the viability of cancer cells and cancer stem cells according to the treatment of the pharmaceutical composition containing trimebutine of the present invention or the $BK_{Ca}$ channel blocker or the Na channel blocker of Comparative Example. The specific experimental method is the same as the cell viability analysis method described in Experimental Protocol 1, and the results are shown in FIGS. 4A and 4B.

Figure 4A:
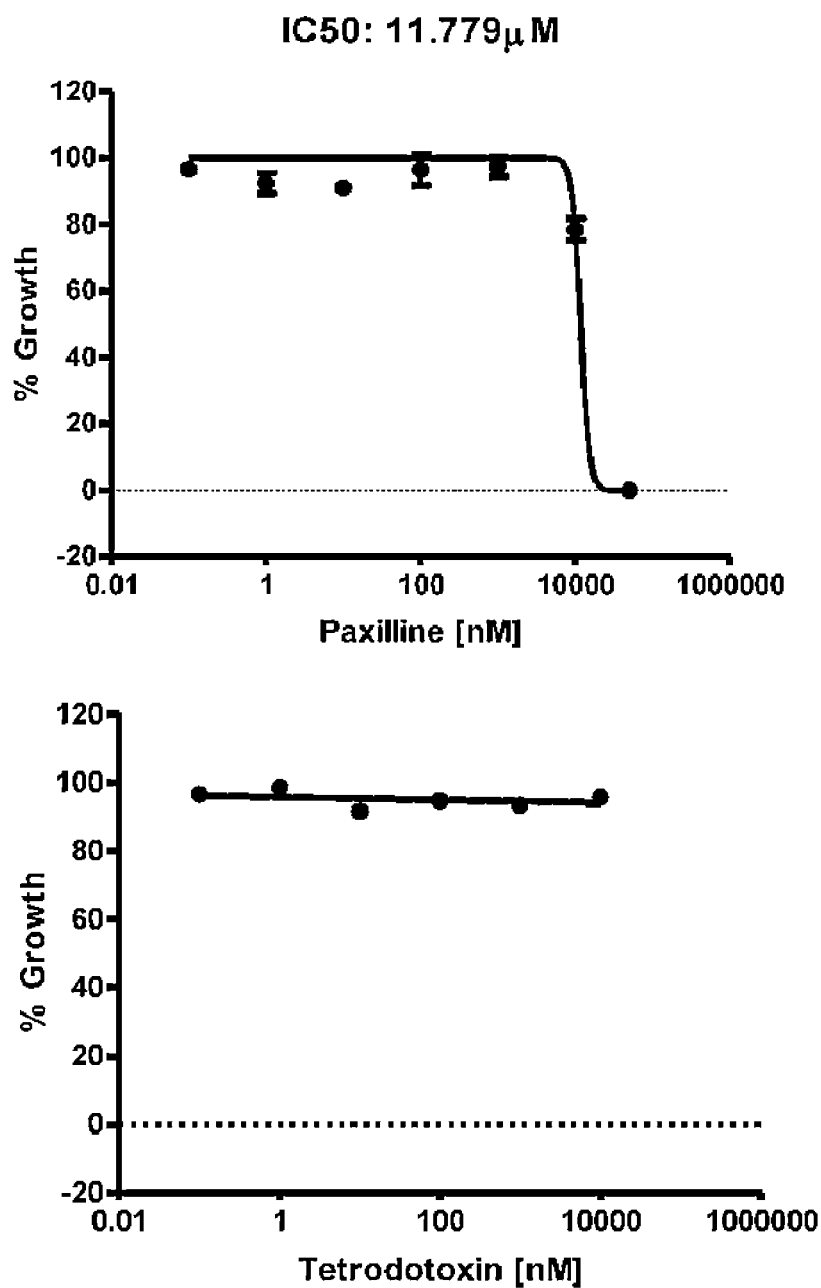
FIG. 4A is a set of diagrams showing the dose-response curves of A2780 cell viability when the pharmaceutical composition of Comparative Example 2 was treated.

FIG. 4A is a set of diagrams showing the results of measuring the maximum concentration at the moment when the activity of ovarian cancer cells was reduced by half and the dose-response curves of A2780 cell viability when the compound of Comparative Example 2 was treated. The experiment was performed with 3000 cells for 3 days by the Cell titer Glo method.

Figure 4B:
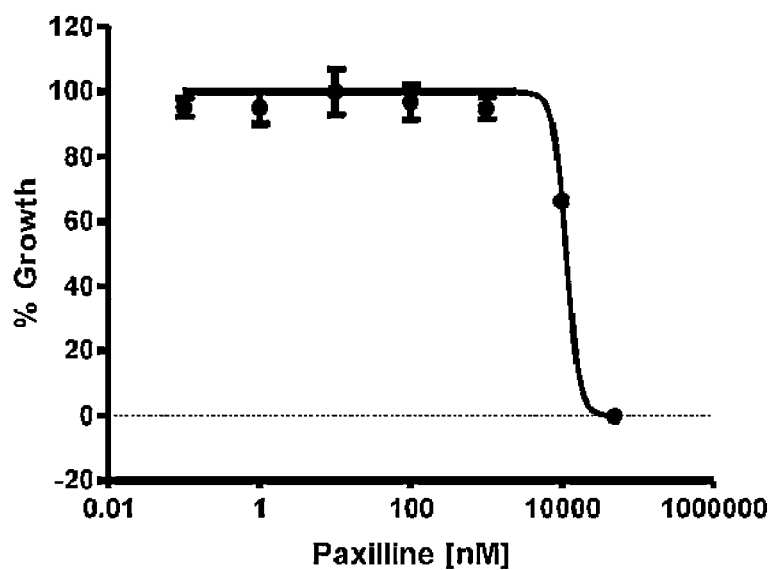
FIG. 4B is a set of diagrams showing the dose-response curves of A2780-SP cell viability when the pharmaceutical composition of Comparative Example 2 was treated.
Figure 4B:
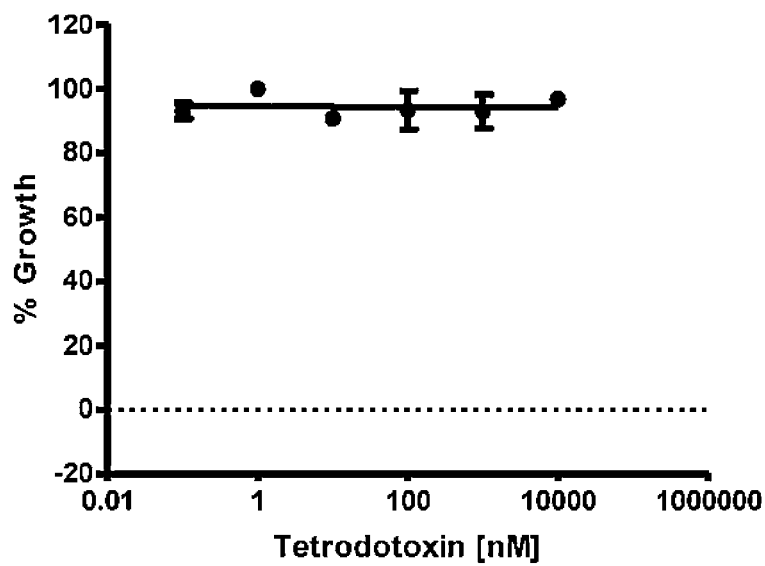

FIG. 4B is a set of diagrams showing the results of measuring the maximum concentration at the moment when the activity of ovarian cancer cells was reduced by half and the dose-response curves of A2780-SP cell viability when the compound of Comparative Example 2 was treated. The experiment was performed with 1500 cells for 7 days by the Cell titer Glo method.

As shown in FIGS. 4A and 4B, it was confirmed that the viability of cancer cells and cancer stem cells was not affected by suppressing $BK_{Ca}$ or Na channel alone.

<2-3> Analysis of Cancer Cell and Cancer Stem Cell Growth Inhibition by Simultaneous Use of $BK_{Ca}$, Na and Ca Channel Blockers Trimebutine of the present invention has the effect of inhibiting not only Ca channel but also $BK_{Ca}$ and Na channels, so an experiment was conducted to confirm whether inhibiting the channels at the same time is more effective in inhibiting cancer stem cell growth than inhibiting each channel alone.

Figure 5A:
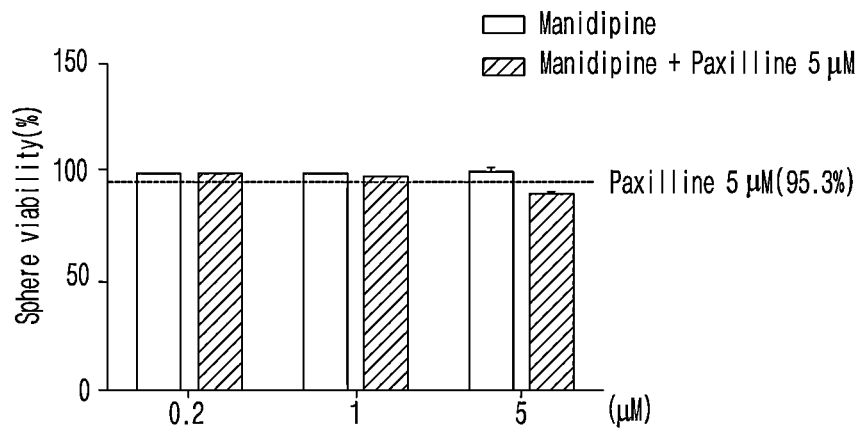
FIGS. 5A to 5D are diagrams showing the cell viability of A2780 cells when the pharmaceutical composition containing manidipine of Comparative Example 1 and the pharmaceutical composition of Comparative Example 2 were treated.
Figure 5B:
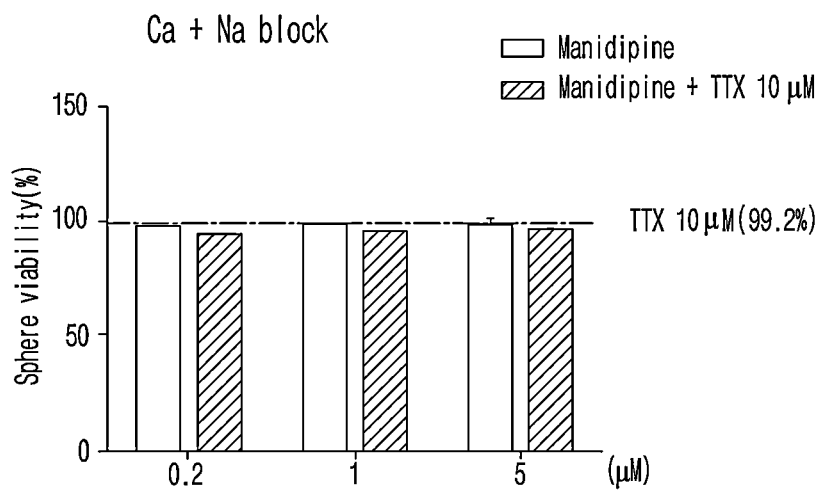
Figure 5C:
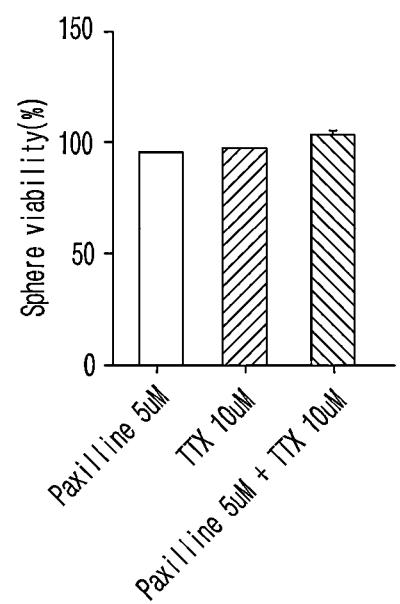
Figure 5D:
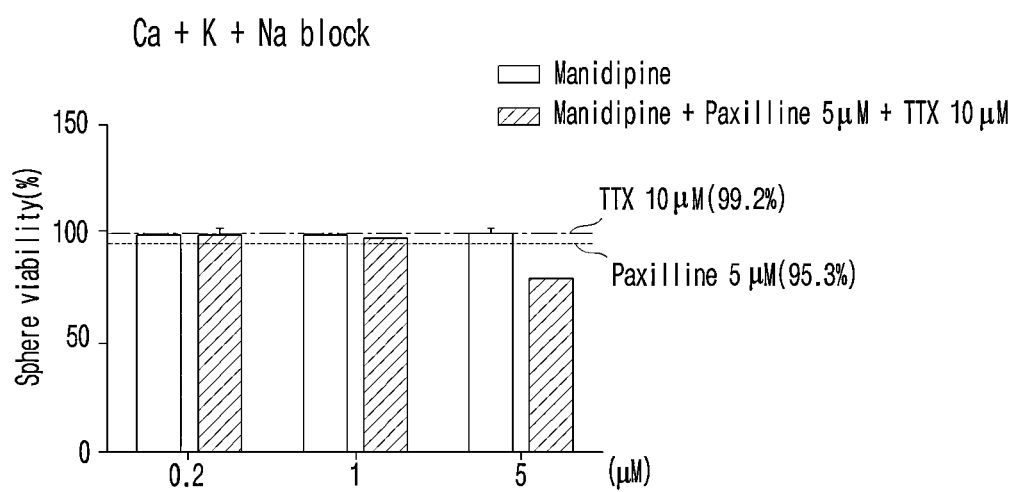

For the experiment, manidipine (Ca channel blocker) of Comparative Example 1, Paxilline ($BK_{Ca}$ channel blocker) and Tetrodotoxin (Na channel blocker) of Comparative Example 2 were prepared. The specific experimental method is the same as the cell viability analysis method described in Experimental Protocol 1, and the results are shown in FIGS. 5A and 5B.

FIGS. 5A to 5D are diagrams showing the cell viability of A2780 cells when the pharmaceutical composition comprising one or more of manidipine (Ca channel blocker) of Comparative Example 1, Paxilline ($BK_{Ca}$ channel blocker) and Tetrodotoxin (Na channel blocker) of Comparative Example 2 was treated. The experiment was performed with 3000 cells for 3 days by the Cell titer Glo method.

Figure 6A:
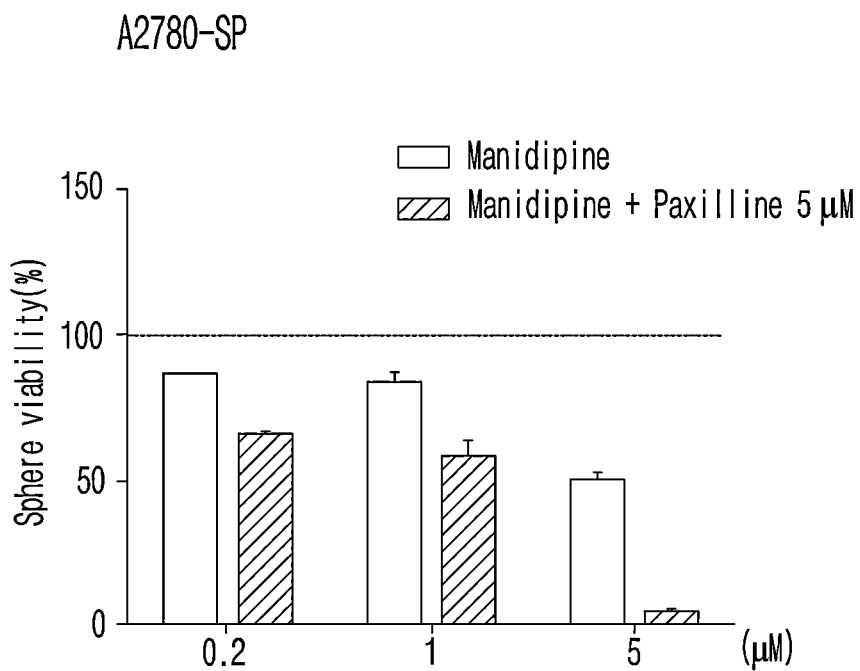
Figure 6B:
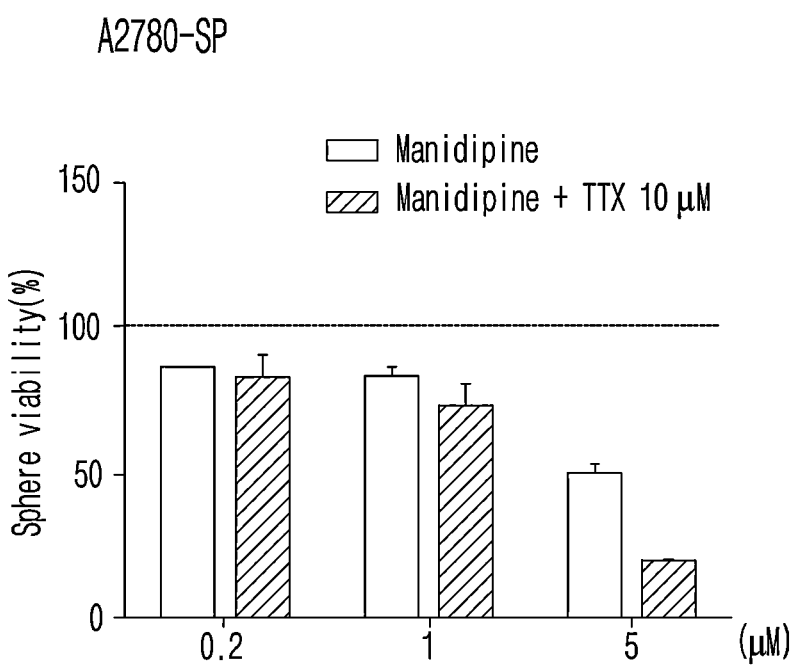

FIGS. 6A to 6C are diagrams showing the cell viability of A2780-SP cells when the pharmaceutical composition comprising one or more of manidipine (Ca channel blocker) of Comparative Example 1, Paxilline ($BK_{Ca}$ channel blocker) and Tetrodotoxin (Na channel blocker) of Comparative Example 2 was treated. The experiment was performed with 1500 cells for 7 days by the Cell titer Glo method.

As shown in FIGS. 5A to 5D, it was confirmed that the simultaneous inhibition of two or more channels in A2780 cells did not affect the viability of cancer cell.

As shown in FIGS. 6A to 6C, it was confirmed that the simultaneous inhibition of two channels, particularly Ca channel and $BK_{Ca}$ channel, further promoted apoptosis.

Therefore, since trimebutine can simultaneously inhibit Ca, Na and $BK_{Ca}$ channels, it can be seen that it shows good activity in inhibiting cancer stem cells and has a selective anticancer effect on cancer stem cells.

Figure 7A:
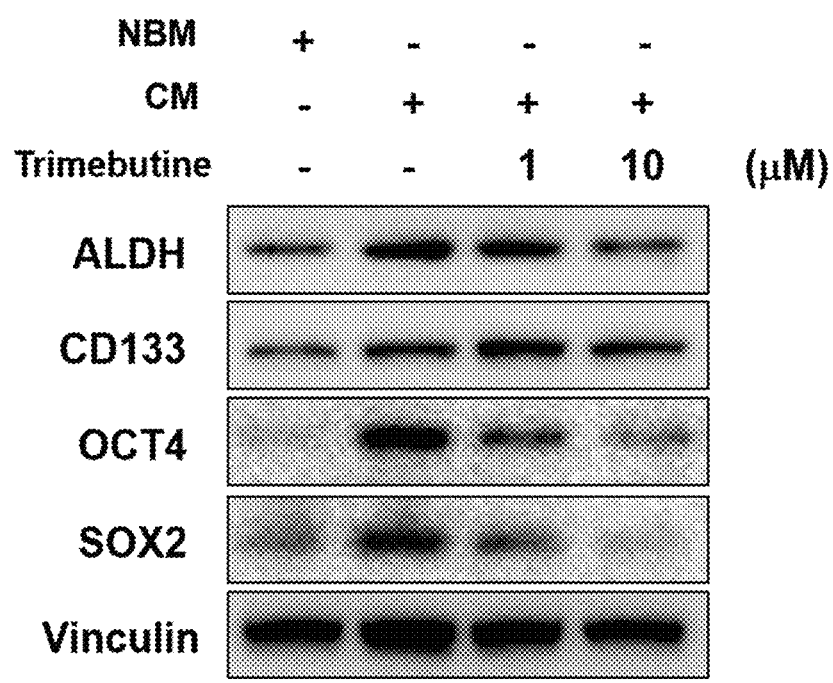
FIG. 7A is an image showing the results of observing the expression changes of the markers related to cancer stemness in ovarian cancer stem cells (A2780-SP) when the pharmaceutical composition of Example was treated.
Figure 7B:
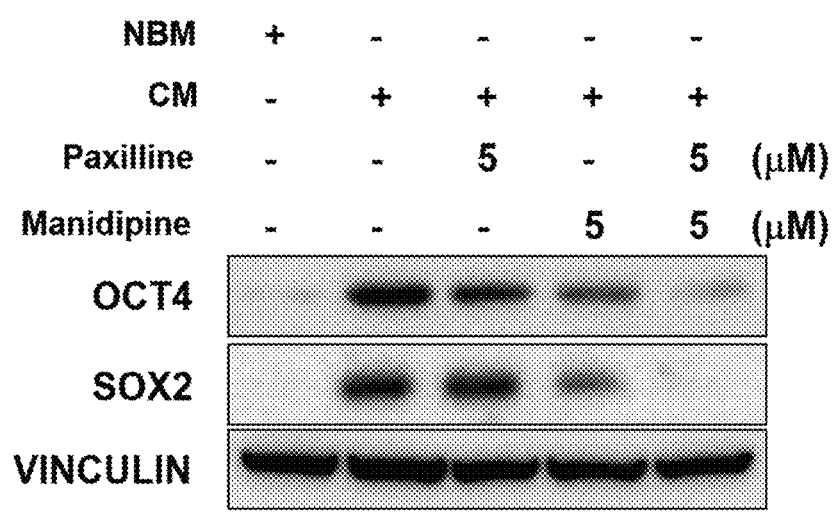
FIG. 7B is an image showing the results of observing the expression changes of the markers related to cancer stemness in ovarian cancer stem cells (A2780-SP) when manidipine of Comparative Example 1, a Ca channel blocker, and Paxilline of Comparative Example 2, a $BK_{Ca}$ channel blocker, were treated.

Experimental Example 3: Expression Analysis of Stemness, Survival and Growth Related Factors In order to confirm the anticancer effect through the changes in the expressions of the markers related to stemness and the proteins related to survival and proliferation of cancer stem cells according to the treatment of the pharmaceutical composition containing trimebutine of the present invention, the expression levels of various factors were analyzed by Western blotting. The results are shown in FIGS. 7A and 7B. The specific experimental method is the same as the Western blotting method described in Experimental Protocol 3. In FIG. 7B, Paxilline of Comparative Example 2 and manidipine of Comparative Example 1 were tested in the same manner as the Western blotting described in Experimental Protocol 3 except that 5 μM of Paxilline of Comparative Example 2 and manidipine of Comparative Example 1 was treated.

FIG. 7A is an image showing the results of observing the expression changes of the markers related to cancer stemness in ovarian cancer stem cells (A2780-SP) when the pharmaceutical composition of Example was treated.

FIG. 7B is an image showing the results of observing the expression changes of the markers related to cancer stemness in ovarian cancer stem cells (A2780-SP) when manidipine of Comparative Example 1, a Ca channel blocker, and Paxilline of Comparative Example 2, a $BK_{Ca}$ channel blocker, were treated separately or simultaneously.

As shown in FIG. 7A, the expressions of ALDH, OCT4 and SOX2, the markers related to cancer stemness, were reduced when the pharmaceutical composition of Example 1 was treated. As shown in FIG. 7B, the effect of reducing the expressions of the markers related to cancer stemness were further increased when the $BK_{Ca}$ channel blocker and the Ca channel blocker were used together to simultaneously inhibit $BK_{Ca}$ channel and Ca channel. From the above results, it was confirmed that the pharmaceutical composition of the present invention inhibited $BK_{Ca}$ channel and Ca channel at the same time to suppress stemness very effectively.

Figure 8A:
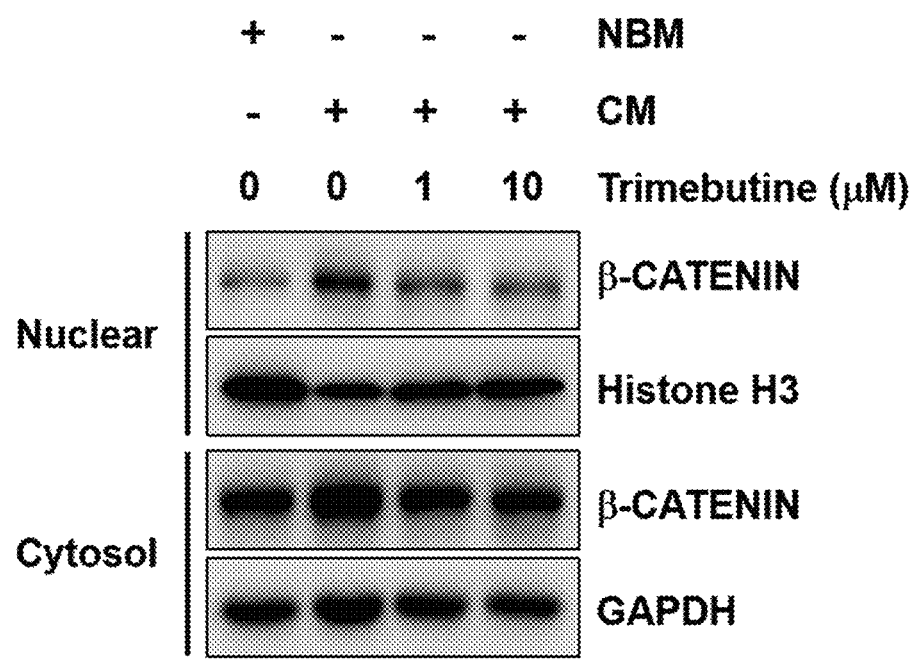
FIGS. 8A and 8C are images showing the results of observing the changes of β-catenin S552 phosphorylation degree in ovarian cancer stem cells (A2780-SP) when the pharmaceutical composition of Example was treated.
Figure 8B:
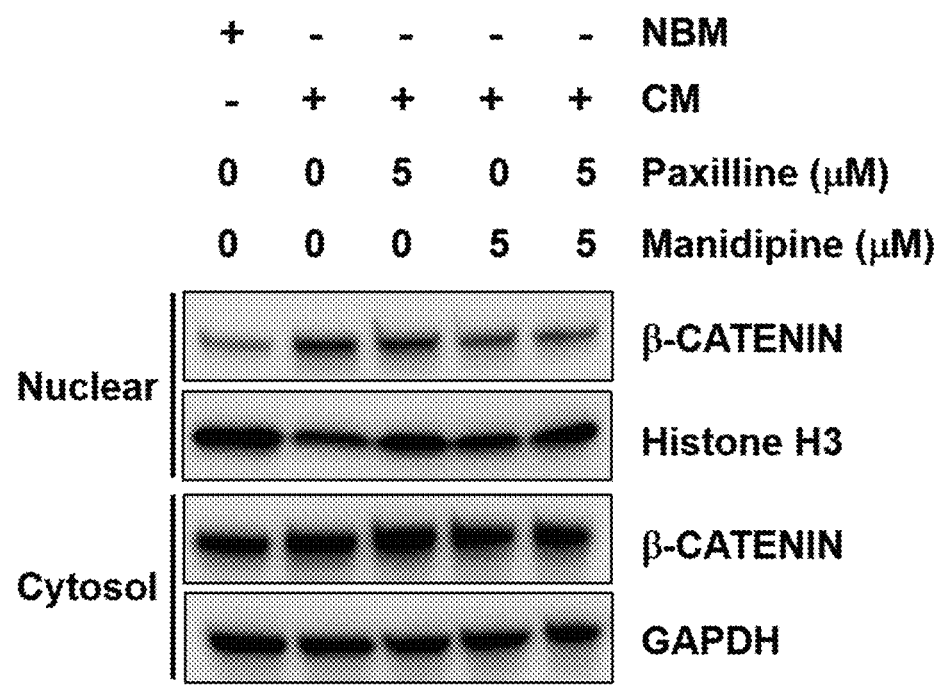
FIGS. 8B and 8D are images showing the results of observing the degree of translocation of β-catenin into the nucleus and the degree of β-catenin S552 phosphorylation when manidipine of Comparative Example 1, a Ca channel blocker, and Paxilline of Comparative Example 2, a $BK_{Ca}$ channel blocker, were treated individually or simultaneously.

Experimental Example 4: Analysis of β-Catenin Signaling Inhibition and Stemness Inhibition Effect Through Changes of β-Catenin Translocation and Phosphorylation Levels In order to confirm the inhibition of wnt/β-catenin signaling, which plays an important role in maintaining stemness according to the treatment of the pharmaceutical composition containing trimebutine of the present invention, the degree of translocation of β-catenin into the nucleus and the degree of phosphorylation at S552 associated with the enhanced transcriptional ability of β-catenin were analyzed by Western blotting. The results are shown in FIGS. 8A to 8B. The specific experimental method is the same as the Western blotting method described in Experimental Protocol 3. In FIGS. 8B and 8D, Paxilline of Comparative Example 2 and manidipine of Comparative Example 1 were tested in the same manner as the Western blotting described in Experimental Protocol 3 except that 5 μM of Paxilline of Comparative Example 2 and manidipine of Comparative Example 1 was treated.

Figure 8C:
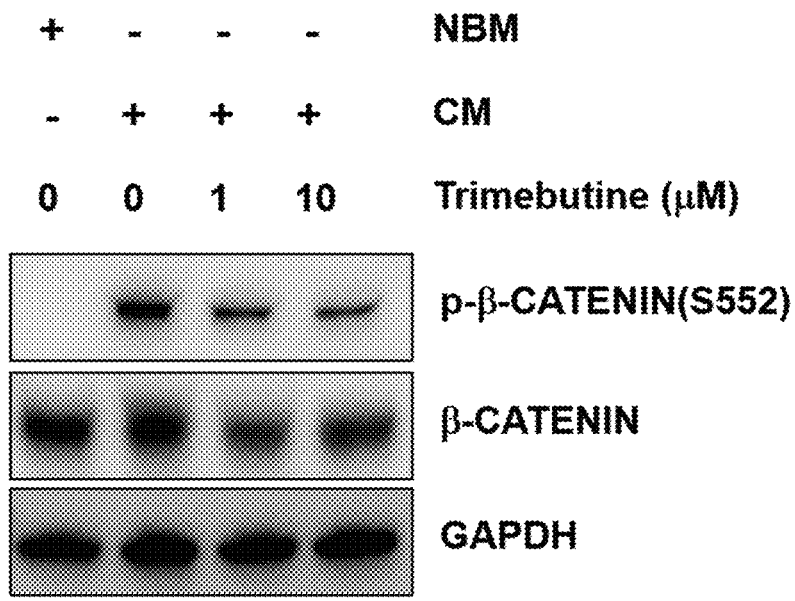
Figure 8D:
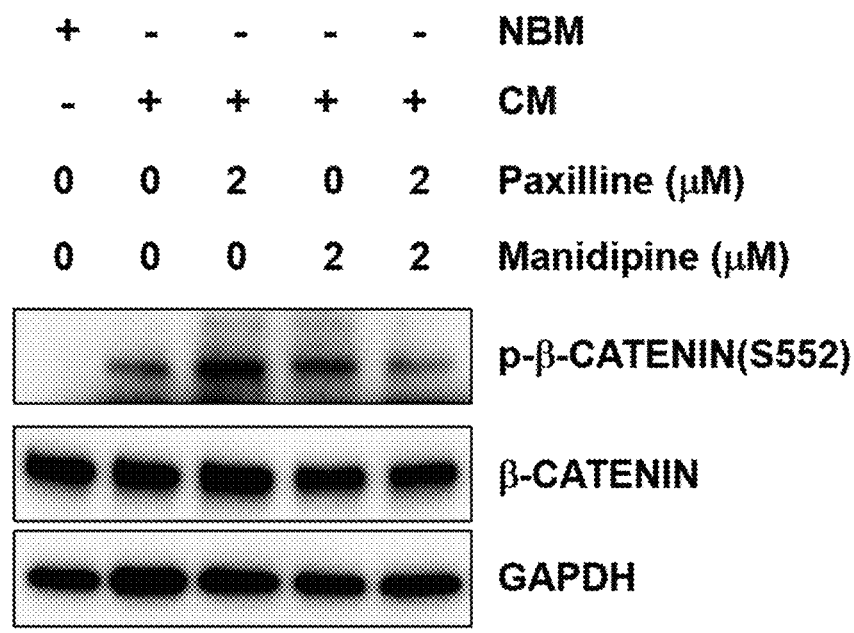

FIGS. 8A and 8C are images showing the results of observing the changes in the degree of translocation of β-catenin into the nucleus and the degree of β-catenin S552 phosphorylation in ovarian cancer stem cells (A2780-SP) when the pharmaceutical composition of Example was treated.

FIGS. 8B and 8D are images showing the results of observing the degree of translocation of β-catenin into the nucleus and the degree of β-catenin S552 phosphorylation when manidipine of Comparative Example 1, a Ca channel blocker, and Paxilline of Comparative Example 2, a $BK_{Ca}$ channel blocker, were treated individually or simultaneously.

As shown in FIGS. 8A and 8C, the translocation of β-catenin into the nucleus and the degree of β-catenin S552 phosphorylation were reduced when the pharmaceutical composition of Example 1 was treated. As shown in FIGS. 8B and 8D, the effect of reducing the degree of translocation of β-catenin into the nucleus and the degree of β-catenin S552 phosphorylation was further increased when the $BK_{Ca}$ channel blocker and the Ca channel blocker were used together to simultaneously inhibit $BK_{Ca}$ channel and Ca channel. From the above results, it was confirmed that the pharmaceutical composition of the present invention inhibited $BK_{Ca}$ channel and Ca channel at the same time to suppress wnt/β-catenin signaling and stemness very effectively.

Experimental Example 5: Animal Model Experiment

Figure 9A:
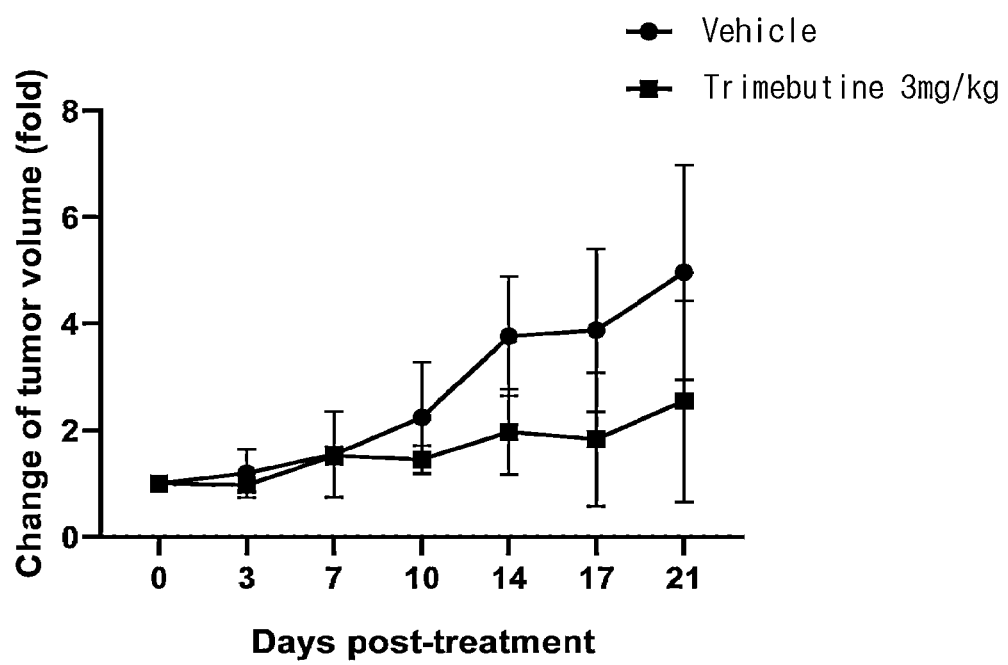
FIG. 9A is a graph showing the results of evaluating the tumor formation inhibitory effect when the pharmaceutical composition of Example was treated in the A2780-SP xenograft model.
Figure 9B:
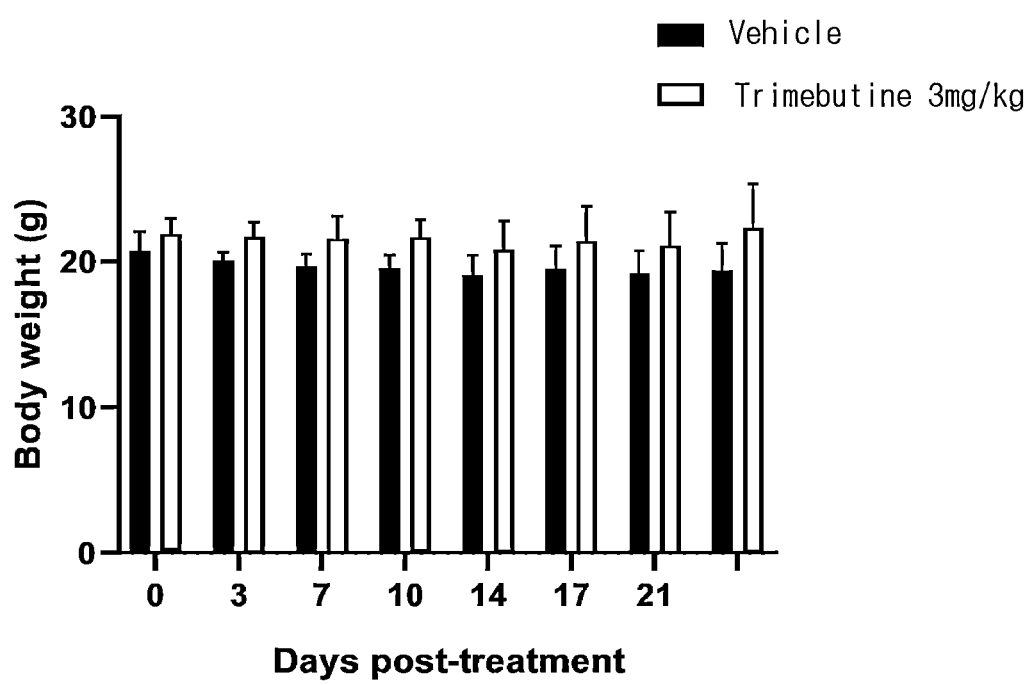
FIG. 9B is a graph showing the results of measuring the change in body weight of the animal model when the pharmaceutical composition of Example was treated in the A2780-SP xenograft model.

In order to confirm the ovarian cancer treatment effect of the pharmaceutical composition containing trimebutine of the present invention in vivo, an animal model experiment was performed. The results are shown in FIGS. 9A and 9B. The specific experimental method is the same as the animal experiment method described in Experimental Protocol 5.

FIG. 9A is a graph showing the results of evaluating the tumor formation inhibitory effect when the pharmaceutical composition of Example was treated in the A2780-SP xenograft model.

FIG. 9B is a graph showing the results of measuring the change in body weight of the animal model when the pharmaceutical composition of Example was treated in the A2780-SP xenograft model.

As shown in FIG. 9A, the pharmaceutical composition containing trimebutine of the present invention specifically inhibited tumor formation in ovarian cancer stem cells. As shown in FIG. 9B, there was no change in body weight by the pharmaceutical composition containing trimebutine of the present invention. From the above results, it was confirmed that the pharmaceutical composition of the present invention was non-toxic.

Through the Experimental Examples above, it can be seen that the pharmaceutical composition containing trimebutine of the present invention can be effectively used as a pharmaceutical composition for preventing or treating ovarian cancer by inhibiting ovarian cancer recurrence, metastasis and progression.

As mentioned above, the present invention has been described in detail through the preferred preparative examples, examples and experimental examples, but the scope of the present invention is not limited to the specific examples, and should be interpreted by the appended claims. In addition, those of ordinary skill in the art should understand that many modifications and variations are possible without departing from the scope of the present invention.

Industrial Applicability

The pharmaceutical composition comprising trimebutine of the present invention is excellent in inhibiting growth and proliferation of cancer stem cells even when used alone, and thus can suppress the recurrence, metastasis, and progression of cancer. Therefore, the composition can be effectively used as a pharmaceutical composition for prevention or treatment of cancer or in combination with other agents.

What is claimed is:

1. A method for treating ovarian cancer comprising administering a compound represented by formula 1 below, a stereoisomer thereof, a hydrate thereof, or a pharmaceutically acceptable salt thereof as an active ingredient,
wherein the ovarian cancer is characterized by the presence of ovarian cancer stem cells and the compound is administered in an amount sufficient to inhibit the proliferation of the ovarian cancer stem cells:

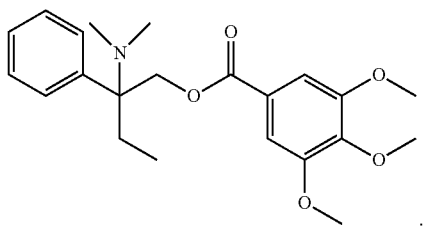

[Formula 1]

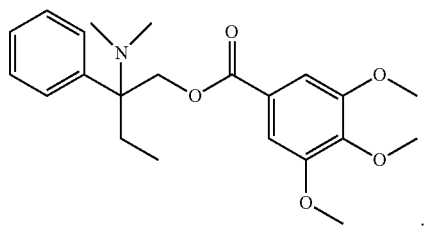

[Formula 1]

2. The method for treating ovarian cancer according to claim 1, wherein the compound inhibits the proliferation of ovarian cancer stem cells.

3. The method for treating ovarian cancer according to claim 1, wherein the compound inhibits the expression of at least one selected from the group of proteins consisting of CT3/4, NANOG, SOX2, ALDH, OCT4, CD133, pAKT, AKT, p-ERK, ERK, p-p38 and p38.

4. A method for treating ovarian cancer comprising administering a combination preparation comprising a compound represented by formula 1 below, a stereoisomer thereof, a hydrate thereof, or a pharmaceutically acceptable salt thereof and an anticancer agent,
wherein the ovarian cancer is characterized by the presence of ovarian cancer stem cells and the compound is administered in an amount sufficient to inhibit the proliferation of the ovarian cancer stem cells:

5. The method for treating ovarian cancer according to claim 4, wherein the combination preparation inhibits the proliferation of ovarian cancer stem cells.

6. The method for treating ovarian cancer according to claim 4, wherein the anticancer agent is at least one selected from the group consisting of doxorubicin, paclitaxel, vincristine, daunorubicin, vinblastine, actinomycin-D, docetaxel, etoposide, teniposide, bisantrene, homoharringtonine, imatinib, cisplatin, 5-fluorouracil, methotrexate, busulfan, chlorambucil, cyclophosphamide, melphalan, nitrogen mustard and nitrosourea.

7. The method for treating ovarian cancer according to claim 5, wherein the combination preparation inhibits the expression of at least one selected from the group of proteins consisting of CT3/4, NANOG, SOX2, ALDH, OCT4, CD133, pAKT, AKT, p-ERK, ERK, p-p38 and p38.

* * * * *